US010086078B2

(12) United States Patent
Ahuja et al.

(10) Patent No.: US 10,086,078 B2
(45) Date of Patent: *Oct. 2, 2018

(54) FAST DISSOLVING PHARMACEUTICAL COMPOSITION

(75) Inventors: Varinder Ahuja, Mumbai (IN); Tejas Gunjikar, Nashik (IN); Kristin Wannerberger, Pully (CH)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/638,121

(22) PCT Filed: Mar. 28, 2011

(86) PCT No.: PCT/EP2011/054698
§ 371 (c)(1),
(2), (4) Date: Jan. 29, 2013

(87) PCT Pub. No.: WO2011/120903
PCT Pub. Date: Oct. 6, 2011

(65) Prior Publication Data
US 2013/0123180 A1 May 16, 2013

(30) Foreign Application Priority Data
Mar. 29, 2010 (IN) .............................. 742/DEL/2010

(51) Int. Cl.
| | | |
|---|---|---|
| A61K 47/36 | (2006.01) |
| A61K 9/00 | (2006.01) |
| A61K 9/19 | (2006.01) |
| A61K 31/426 | (2006.01) |
| A61K 31/4545 | (2006.01) |
| A61K 31/47 | (2006.01) |
| A61K 38/11 | (2006.01) |
| C07K 7/50 | (2006.01) |

(52) U.S. Cl.
CPC ............ *A61K 47/36* (2013.01); *A61K 9/0056* (2013.01); *A61K 9/19* (2013.01); *A61K 31/426* (2013.01); *A61K 31/4545* (2013.01); *A61K 31/47* (2013.01); *A61K 38/11* (2013.01); *A23V 2250/5062* (2013.01); *C07K 7/50* (2013.01)

(58) Field of Classification Search
CPC ........ A23V 2250/5062; A23V 2200/22; A23V 2250/24; A23V 2250/64; A23V 2200/228; A61K 9/2018; A61K 9/0056; A61K 9/1623; A61K 9/1694; A61K 9/19; A61K 9/4891; A61K 9/1075; A61K 9/1682; A23L 1/097; A23L 1/0047; A23L 1/005; A23L 1/0052
See application file for complete search history.

(56) References Cited

U.S. PATENT DOCUMENTS

| | | | |
|---|---|---|---|
| 4,260,602 A | 4/1981 | Moreno | |
| 6,509,040 B1 * | 1/2003 | Murray et al. ................ | 424/489 |
| 6,911,217 B1 | 6/2005 | Gren et al. | |
| 7,560,429 B2 | 7/2009 | Nilsson et al. | |
| 8,007,830 B2 | 8/2011 | Down | |
| 8,158,152 B2 | 4/2012 | Palepu | |
| 8,946,153 B2 * | 2/2015 | Gupta et al. ................ | 514/10.9 |
| 9,096,335 B2 | 8/2015 | Ahuja et al. | |
| 2002/0177561 A1 | 11/2002 | Van Loo et al. | |
| 2004/0096569 A1 | 5/2004 | Barkalow et al. | |
| 2005/0266088 A1 | 12/2005 | Hinrichs et al. | |
| 2008/0044900 A1 | 2/2008 | Mooney et al. | |
| 2008/0241226 A1 | 10/2008 | Abeln et al. | |
| 2009/0246257 A1 | 10/2009 | Modi | |
| 2010/0069320 A1 | 3/2010 | Speelmans | |
| 2012/0135050 A1 | 5/2012 | Dill | |
| 2013/0123179 A1 | 5/2013 | Ferring | |
| 2013/0310319 A1 | 11/2013 | Ferring | |

FOREIGN PATENT DOCUMENTS

| | | | |
|---|---|---|---|
| CA | 2516291 | 9/2014 | |
| CN | 1094282 A | 11/1994 | |
| CN | 1337876 | 2/2002 | |
| EP | 0958825 A1 * | 11/1999 | ............ A61K 31/70 |
| EP | 1308171 | 5/2003 | |
| EP | 1428526 A1 | 6/2004 | |
| EP | 1514553 | 3/2005 | |
| EP | 1501534 | 7/2006 | |
| EP | 1757279 | 2/2007 | |
| GB | 1 548 022 | 7/1979 | |
| JP | 2006/511549 | 4/2006 | |
| WO | WO 00/25754 | 5/2000 | |
| WO | WO 00/27364 | 5/2000 | |
| WO | WO 00/44351 | 8/2000 | |
| WO | WO2000061117 A1 | 10/2000 | |
| WO | WO 00/78817 A1 * | 12/2000 | ............ C08B 37/18 |
| WO | WO 01/00182 | 1/2001 | |

(Continued)

OTHER PUBLICATIONS

DDAVP Nasal Spray (desmopressin acetate) 2007. Sanofi-Aventis U.S. LLC.*
TEVA Pharmaceuticals USA. Desmopressin Acetate Tablet product Description (Feb. 2008).*
Eissens et al. Inulin as filler-binder for tablets prepared by direct compaction. European Journal of Pharmaceutical Sciences 15 (2002) 31-38.*
An International Search Report and Written Opinion dated Mar. 9, 2012, which issued in corresponding International Application Serial No. PCT/EP2011/054698.
An International Preliminary Report on Patentability dated Oct. 2, 2012, which issued in corresponding International Application Serial No. PCT/EP2011/054698.

(Continued)

*Primary Examiner* — Marcela M Cordero Garcia
*Assistant Examiner* — Jia-Hai Lee
(74) *Attorney, Agent, or Firm* — Finnegan, Henderson, Farabow, Garrett & Dunner, LLP

(57) ABSTRACT

The subject invention is directed to a pharmaceutical composition comprising an open matrix network carrying a pharmaceutically active ingredient, wherein the open matrix network comprises inulin.

38 Claims, No Drawings

(56) References Cited

FOREIGN PATENT DOCUMENTS

| WO | WO 01/12161 A1 * | 2/2001 | ............... A61K 9/20 |
| --- | --- | --- | --- |
| WO | WO 2002/03992 | 1/2002 | |
| WO | WO 2003/082246 | 10/2003 | |
| WO | WO 03/094886 A2 * | 11/2003 | ............... A61K 9/00 |
| WO | WO 2003/094886 A2 | 11/2003 | |
| WO | WO 2004/054546 A1 * | 7/2004 | ............... A61K 9/19 |
| WO | WO 2006/047738 | 5/2006 | |
| WO | WO 2006/067593 A1 * | 6/2006 | ............... A61K 9/00 |
| WO | WO 2007/143676 | 12/2007 | |
| WO | WO 2009/093785 A1 | 7/2009 | |
| WO | WO 2011/120904 A2 | 10/2011 | |
| WO | WO 2013/037708 | 3/2013 | |

OTHER PUBLICATIONS

Srinarong et al., "Strongly enhanced dissolution rate of fenofibrate solid dispersion tablets by incorporation of superdisintegrants", EP Journal of Pharmaceutics and Biopharmaceutics, Elsevier, 73(1):154-161 (Sep. 2009).

EPO Official Action dated Dec. 4, 2013 issued in corresponding EP Application No. 11711526.1-1455.

EPO Official Action issued in corresponding EP Application No.11711321.7-1455 dated Jun. 4, 2015.

Krasnyuk et al., Farmatsevticheskaya technologiya; Technologiya lekarstvnnykh form: Uchebnik diya stud. Sred. Prof. ucheb, Zavedeniy, -M: Akademiya, pp. 464 (2004).

Russian Office Action dated May 21, 2015, in Russian Application No. 2012141140/15(066314).

Beine et al., "Directed Optimization of Biocatalytic Transflycosylation Processes by the Integration of Genetic Algorithms and Fermentative Approaches into a Kinetic Model", Process Biochemistry, Elsevier, NL, vol. 44, No. 10, pp. 1103-1114 (2009).

Combie, J., "Polysaccharides for Drug Delivery and Pharmaceutical Applications", Chapter 3, pp. 263-269, ISBN13: 9780841239609 (2006).

Co-pending U.S. Appl. No. 13/636,758, filed Jan. 29, 2013 (Published May 16, 2013 as US 2013-0123179 A1).

Co-pending U.S. Appl. No. 13/952,084, filed Jul. 25, 2013 (Published Nov. 21, 2013, US 2013-0310319 A1).

International Preliminary Report on Patentability for PCT/EP2011/054699 dated Oct. 2, 2012.

International Search Report and Written Opinion for PCT/EP2011/054699 dated Oct. 2, 2012.

Office Action (Final) dated May 8, 2014, in co-pending U.S. Appl. No. 13/952,084.

Office Action dated May 8, 2014, in co-pending U.S. Appl. No. 13/636,758.

Pleuvry, Barbara J., "Drugs Acting by Causing Physicochemical Changes in the Enviornment Anesthesia & Intensive Care Medicine," vol. 6, Issue 4, pp. 133-134, (Apr. 2005).

Shih et al., "Selective Production and Characterization of Levan by *Bacillus subtillis* (Natto) Takahashi," J. Agric Food Chem. Oct. 19, 2005;53(21):8211-5.

Sugimoto et al., "Effect of Formulated Ingredients on Rapidly Disintegrating Oral Tablets Perpared by the Crystalline Transition Method", Chem Pharm Bull (Tokyo), 54(2):175-80, Feb. 2006.

Office Action (non-final) dated Sep. 10, 2015, U.S. Appl. No. 14/343,285.

References Office Action dated Dec. 4, 2015, U.S. Appl. No. 14/571,883.

Office Action (non-final) dated May 13, 2016, U.S. Appl. No. 14/343,285.

Raes et al., "Retrospective Analysis of Efficacy and Tolerability of Tolterodine in Children with Overactive Bladder," European Urology 45 (2004) pp. 240-244.

Tsujimura et al., "Survey of Overactive Bladder Symptoms Influencing Bother Before and After Treatment With Tamsulosin Hydrochloride in Japanese Patients With Benign Prostatic Hyperplasia," Urology 78, 2011, pp. 1058-1062.

Chueshov et al., "Promyshlennaya tekhnologia lekarstv," UkrFA, Kharkov, Osnova, 1999, vol. 2. p. 353.

Office Action (final) dated Feb. 9, 2017, U.S. Appl. No. 14/443,759.

Office Action (non-final) dated Mar. 23, 2017, U.S. Appl. No. 14/571,883.

The Committee for Establishment of the Clinical Guidelines for Nocturia of the Neurogenic Bladder Society, "Clinical guidelines for nocturia," Int. J. Urology, 2010, vol. 17, pp. 397-409.

Merck Index Online (Ondansetron). Https://www.rsc.org/Merck-Index/monograph/m8213/ondansetron?q=authorize Nov. 18, 2017.

Office Action dated Dec. 8, 2017, in co-pending U.S. Appl. No. 14/571,883.

* cited by examiner

FAST DISSOLVING PHARMACEUTICAL COMPOSITION

CROSS REFERENCE TO PRIOR APPLICATIONS

This is a U.S. National Phase application under 35 U.S.C. § 371 of International Patent Application No. PCT/EP2011/054698, filed Mar. 28, 2011, and claims the priority of Indian Patent Application No. 742/DEL/2010, filed Mar. 29, 2010 both of which are incorporated by reference herein in their entirety. The International Application published in English on Oct. 6, 2011 as WO 2011/120903 under PCT Article 21(2).

FIELD OF THE INVENTION

The subject invention relates to fast dissolving pharmaceutical compositions, to methods of making them and to their use in the treatment and prophylaxis of diseases in mammals, particularly humans.

BACKGROUND OF THE INVENTION

Fast dissolving pharmaceutical dosage forms which are designed to release an active ingredient in the oral cavity are well known and can be used to deliver a wide range of drugs (*Critical Reviews in Therapeutic Drug Carrier Systems*, 21(6):433-475 (2004); Seager H. (1998), *J. Phar. Pharmacol* 50:375-382; Bandari et al. (January 2008), *Asian Journal of Pharmaceutics* 2-11).

In a fast dissolving dosage form, a drug may physically be trapped in a matrix composed of e.g. mannitol and fish gelatin (EP 1501534; EP1165053), modified starch (U.S. Pat. No. 6,509,040), pullulan in combination with an amino acid (EP1803446), or maltodextrin in combination with sorbitol (US2004/0228919). The solution, suspension or dispersion of the drug and the carrier material may be filled into blister cavities, frozen and thereafter lyophilized. As any product of technology at all times, also the latter can still be improved upon.

The subject invention provides an improved fast-dispersing dosage form.

SUMMARY OF THE INVENTION

The subject invention provides a new fast dissolving oral pharmaceutical composition typically in a unit dosage form, typically an oral lyophilisate (also named orally disintegrating tablet).

In one embodiment, the present invention provides a pharmaceutical composition comprising an open matrix network carrying a pharmaceutically active ingredient, wherein the open matrix network is comprised of inulin.

In another embodiment the present invention provides a pharmaceutical composition comprising a matrix carrying a pharmaceutically active ingredient, the matrix rapidly disintegrating upon contact with an aqueous solution or with saliva, said matrix comprising inulin.

The pharmaceutical composition of the invention is unique in that it has a rapid dissolution in aqueous medium or in saliva, in particular the composition rapidly disintegrates when taken orally. The disintegration in an aqueous medium or in the oral cavity upon consumption (where it disintegrates upon contact with saliva) is typically within less than 10 seconds, and at times less than 9, 8, 7, 6, 5, 4, 3, 2 or even 1 seconds.

Accordingly, the subject invention provides a pharmaceutical composition comprising a pharmaceutically active ingredient, having a rapid dissolution rate such that at least 80% of the composition is disintegrated in an aqueous medium or in saliva in less than 10 seconds. In a further embodiment, 90% of the composition is disintegrated in an aqueous medium or in saliva in less than 10 seconds. In yet a further embodiment, 100% of the composition is disintegrated in an aqueous medium or in saliva in less than 10 seconds.

The pharmaceutical composition of the invention may be obtained by subliming a solvent (e.g. water), for example in a freeze drying process, from a liquid preparation that comprises the active ingredient and the matrix forming agent(s) in solution.

According to one embodiment, unit dosage quantities of the liquid preparation that contain a defined amount of active ingredient are introduced into depressions and sublimation is then carried out thereby obtaining (after sublimation) a pharmaceutical composition in a unit dosage form. The depressions may be those of an open blister pack and following the sublimation step, and thereby the formation of the solid unit dosage form of the composition in the depression, a sealing film or foil is placed over the depressions to form a sealed blister pack.

The invention thus provides a process for preparing a pharmaceutical composition that comprises subliming a solvent from a liquid preparation comprising a pharmaceutically active ingredient and inulin in the solvent.

The invention further provides a process for the preparation of a pharmaceutical composition comprising (a) preparing a solution comprising inulin and an active ingredient in a solvent; (b) freezing said solution; (c) subliming the solvent from the frozen solution, wherein the pharmaceutical composition so obtained is in fast-dispersing dosage form which disintegrates within 10 seconds upon contact with an aqueous solution or with saliva.

DETAILED DESCRIPTION OF THE INVENTION

The subject invention provides a fast-dissolving, typically orodispersible, pharmaceutical composition, usually prepared and provided in unit dosage form, typically an oral lyophilisate, comprising an active ingredient and one or more excipients. At least one of the excipients, normally the main matrix forming agent, is the polysaccharide inulin.

The following are some of the terms used above and below in this patent specification and claims:

The terms "active ingredient" or "pharmaceutically active ingredient" will be used interchangeably herein.

The term "pharmaceutical composition" and "composition" are interchangeably used herein to refer to a pharmaceutical composition of the invention. The term "unit dosage form" or "dosage form" will be used herein to refer to said composition which is formulated with an amount of an active pharmaceutical ingredient (API) in a dose for administration as a single dose to a target individual. The unit dosage form may be adapted, depending on the nature of the active ingredient, the indication, the disease stage and various other factors known per se for once, twice, thrice or any other number of daily administrations.

The term "carrying" should be understood to encompass any form of interaction between an active ingredient and the matrix that allows the matrix to hold and/or contain an amount of active ingredient and release it to the medium upon disintegration of the matrix.

The term "matrix" should be understood to denote a solid carrier medium for an active ingredient. The matrix comprises one or more excipients. The excipients that form the matrix may be referred to herein, at times, as "matrix forming agents" and each of said agents as "matrix forming agent".

The term "an open matrix network" should be understood to encompass a matrix of water-soluble or water-dispersible carrier material having interstices dispersed throughout. The matrix rapidly disintegrates upon contact with an aqueous solution or with saliva.

In one embodiment, inulin is the sole matrix forming agent in the composition. In another embodiment, one or more secondary matrix forming agents may be present in the composition.

Non-limiting examples of sugars, sugar alcohols, monosaccharides, disaccharides, trisaccharides, polysaccharides, proteins, amino acids, gums and the like, which are useful as secondary matrix forming agents, include without limitation, mannitol, trehalose, raffinose, pullulan, inositol, sucrose, lactose, dextrose, erythritol, xylitol, lactitol, maltitol, isomalt, alanine, arginine, threonine, glycine, cysteine, serine, histidine, valine, proline, lysine, asparagine, glutamine, ribose, glucose, galactose, fructose, maltose, maltotriose, guargum, xanthan gum, tragacanth gum, veegum and so forth.

Generally, the balance of the formulation can be matrix. Thus the percentage of the inulin matrix can approach 100%. The amount of the secondary matrix forming agent useful in accordance with the present invention may range from about 0 to about 90%.

In one embodiment of the invention, inulin is the main matrix forming agent. In another embodiment, the composition further comprises mannitol or raffinose or trehalose or combinations thereof as secondary matrix forming agent.

In one embodiment, inulin is the matrix forming agent, comprising 10-99.99% out of the entire weight of the composition. In another embodiment, inulin comprises 30-80% out of the entire weight of the composition. In yet another embodiment, inulin comprises 40-75% out of the entire weight of the composition. In yet another embodiment, inulin comprises 50-65% out of the entire weight of the composition.

In other embodiments, mannitol or trehalose or raffinose or combinations thereof are used as secondary matrix forming agents, comprising 0-89.99% out of the entire weight of the composition. In one embodiment, these secondary matrix forming agents comprise 4-50% out of the entire weight of the composition. In another embodiment, these secondary matrix forming agents comprise 25-50% out of the entire weight of the composition.

Thus, a composition of the invention can be one comprising inulin as the main matrix-forming agent and mannitol or trehalose or raffinose (or combinations thereof) as a secondary matrix-forming agent, with inulin constituting 10-99.99% (all % of ingredient are w/w, meaning weight of mentioned ingredient out of the weight of all constituents of the composition combined), and the secondary matrix forming agent constituting 0-89.99%, typically 4-50%. The content of the active ingredient may typically (but not exclusively) be up to 90% of the entire composition, typically in the range of about 0.01-80% depending on the nature of the active ingredient. In one embodiment, the active ingredient comprises 0.01-1% out of the entire weight of the composition. In another embodiment, the active ingredient comprises 0.4-2% out of the entire weight of the composition. In yet another embodiment, the active ingredient comprises 10-25% out of the entire weight of the composition. In other embodiments, the active ingredient comprises 18-40% out of the entire weight of the composition. In yet other embodiments, the active ingredient comprises 60-90% out of the entire weight of the composition.

In one embodiment, the composition of the invention does not contain fish gelatin. In another embodiment, the composition of the invention does not contain a modified starch. In another embodiment, the composition of the invention does not contain pullulan in combination with an amino acid. In another embodiment, the composition of the invention does not contain maltodextrin in combination with sorbitol.

"Disintegration Time" and "Dissolution Time" are used interchangeably herein and should be understood to mean the time needed to dissolve or disintegrate the composition of the invention in an aqueous solution or with saliva within the oral cavity.

"Oral dissolving Time" as used herein should be understood to mean the time needed to dissolve the composition of the invention in the oral cavity.

"Rapid/Fast disintegration/dissolution" as used herein should be understood to encompass disintegration of at least 80% of the composition of the invention, typically 90% and more typically 100% of the composition in an aqueous medium or in saliva (in the oral cavity) within 10 seconds and at times even within 9, 8, 7, 6, 5, 4, 3, 2 or 1 second.

Examples of an aqueous medium as used herein are water or a buffer (e.g. potassium dihydrogen phosphate, dipotassium hydrogen phosphate, sodium hydrogen phosphate) or artificial saliva as described by Morjaria et. al (May 2004), *Dissolution Technologies* 12-15.

Saliva as used herein refers to the saliva in the oral cavity of a mammal, in particular a human.

In one embodiment, a pharmaceutical composition of the invention has a rapid dissolution rate such that at least 80% of the composition is dissolved in an aqueous medium or in saliva within 10 seconds. In another embodiment, a pharmaceutical composition of the invention has a rapid dissolution rate such that at least 90% of the composition is dissolved in an aqueous medium or in saliva within 10 seconds. In yet another embodiment, a pharmaceutical composition of the invention has a rapid dissolution rate such that 100% of the composition is dissolved in an aqueous medium or in saliva within 10 seconds.

The open matrix network enables a liquid to enter the dosage form through the interstices and permeate through its interior. Permeation by aqueous media (such as saliva, water, etc.) exposes the carrier material of both the interior and exterior of the dosage form to the action of the aqueous media whereby the network of carrier material is rapidly disintegrated.

The open matrix structure is of a porous nature and enhances disintegration of the dosage form as compared with ordinary solid shaped pharmaceutical dosage forms such as (granulated and compressed) tablets, pills, capsules, suppositories and pessaries. Rapid disintegration results in rapid release of the active ingredient carried by the matrix.

In the subject invention, the carrier material of the open matrix network is inulin or a derivative thereof.

Inulin is a polymer of fructose $C_6H_{12}O_6$ typically having a terminal glucose. Inulin is a polysaccharide with β-(2->1) linkages between the fructose rings where the numbers describe the carbon atoms in the fructose ring which are linked and the β describes the stereochemical relationship. The inulins are produced by many type of plants.

Inulin as used herein should be understood to encompass inulin derived from any source such as but not limited to plants that contain high concentrations of inulin which include, but are not limited to Elecampane (*Inula helenium*); Dandelion (*Taraxacum officinale*); Wild Yam (*Dioscorea* spp.); Jerusalem artichokes (*Helianthus tuberosus*); Chicory (*Cichorium intybus*); Jicama (*Pachyrhizus erosus*); Burdock (*Arctium lappa*); Onion (*Allium cepa*); Garlic (*Allium sativum*); Agave (*Agave* spp.); Yacón (*Smallanthus sonchifolius* spp.); and Camas (*Camassia* spp.). In a specific embodiment, the Inulin is obtained from Chicory (*Clchorium intybus*).

The pharmaceutically active ingredient may encompass any pharmaceutical ingredient such as a drug, a compound, a peptide, a nucleotide, and so forth.

Non-limiting examples of drugs which can be carried by the open matrix network of the subject invention are analgesics, alpha blockers, anti-allergy, anti-asthma, (allergic rhinitis, chronic uticaria), anti-inflammatory, antacids, anthelmintics, anti-arrhythmic agents, anti-arthritis, anti-bacterial, anti-anxiety, anti-coagulants, anti-depressants, anti-diabetics, anti-diarrheals, anti-diuretics, anti-epileptics, anti-fungal, anti-gout, anti-hypertensive, anti-incontinence, anti-insomnia, anti-malarials, anti-migraine, anti-muscarinic, anti-neoplastic and immunosuppressants, anti-protozoal, anti-rheumatics, anti-rhinitis, anti-spasmatic. anti-thyroid, antivirals, anxiolytics, sedatives, hypnotics and neuroleptics, beta-blockers, anti-benign hyperplasia (BHP), cardiac inotropic, corticosteroids, cough suppressants, cytotoxics, decongestants, diabetic gastric stasis, diuretics, enzymes, anti-parkinsonian, gastro-intestinal, histamine receptor antagonists, infertility, endometriosis, hormone replacement therapy, lipid regulating agents, local anesthetics, neuromuscular agents, nitrates and anti-anginal agents, menstrual disorders, motion sickness, anti-pain, anti-nausea, movement disorders, nutritional agents, opioid analgesics, oral vaccines, proteins, peptides and recombinant drugs, prevention of chemotherapy induced and post operative nausea and vomiting proton pump inhibitors, schizoprenia, sex hormones and contraceptives, seizure/panic disorder, sexual dysfunction (male and female), spermicides, stimulants voiding dysfunctions, veterinary medicines and so forth.

Specific non-limiting examples of these drugs are:

Alfa Blockers: Tamsulosine

Analgesics and anti-inflammatory agents: aspirin, aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac, paracetamol.

Antacids: aluminum hydroxide, magnesium carbonate, magnesium trisilicate, hydrotalcite, dimethicone.

Antihelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-allergic: des loratidine, loratidine, Montelukast, Montelukast sodium, Cetirizin, Fexofenadin, Ebastine.

Anti-arrhythmic agents: amiodarone HCl, disopyramide, flecamide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-diarrheals: atropine sulphate, codeine phosphate, cophenotrope, difenoxin, loperamide hydrochloride, suphasolazine, mesalazine, olsalazine, corticosteroids, prednisolone.

Anti-diuretics: desmopressin, desmopressin acetate.

Anti-epileptics: beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlopidine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl reserpine, terazosin HCl.

Anti-insomnia: Zolpidem

Anti-malaria: amodiaquine, chloroquine, chloroproguanil HCl, halofantrine HCl, mefloquine HCl, proguanil HCl, pyrimethamine, quinine sulphate.

Anti-migraine agents: rizatriptan, dihydroergotamine mesylate, ergotamine tartrate, methysergide maleate, pizotifen maleate, sumatriptan succinate, caffeine.

Anti-muscarinic agents: oxybutinin, tolterodin, atropine, benzhexyl HCl, biperiden, ethopropazine HCl, hyoscine butyl bromide, hyoscyamine, mepenzolate bromide, orphenadrine, oxyphencylcimine HCl, tropicamide.

Anti-neoplastic agents and Immunosuppressants: aminoglutethimide, amsacrine, azathioprene, busulphan, chlorambucil, cyclosporin, dacarbazine, estramustine, etoposide, lomustine, melphalan, mercaptopurine, methotrexate, mitomycin, mitotane, mitoxantrone, procarbazine HO, tamoxifen citrate, testolactone.

Anti-protozoal agents: benznidazole, clioquinol, decoquinate, diiodohydroxyquinoline, diloxanide furcate, dinitolmide, furzolidone, metronidazole, nimorazole, nitrofurazone, omidazole, tinidazole.

Anti-rheumatics: ibuprofen, aceclofenac, acemetacin, azapropazone, diclofenac sodium, diflunisal, etodolac, ketoprofen, indomethacin, mefenamic acid, naproxen, piroxicam, aspirin, benorylate, auranofin, penicillamine.

Anti-rhinitis, anti-uticaria: Cetirizin, fexofenadin, ebastine, loratidin, montelukast Anti-spasmatic: phloroglucinol anhydre Anti-thyroid agents: carbimazole, propylthiouracil.

Antivirals: acyclovir, amantadine hydrochloride, famciclovir, zidovadine, didanosine, zalcitabine, foscarnet sodium.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, Chlorpheniramine, chlormethiazole, chlorpromazine, clobazam, clonazepan, clotiazepam, clozapine, diazepam, droperidol, ethinamate, flunanisone, flunitrazepam, fluoprornazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine phenylephrine, pimozide, prochlorperazine, pseudoephedrineHCL, sulpride, temazepam, thioridazine, triazolam, zopiclone.

β-Blockers: acebutolol, alprenolol, atenolol, labetalol, metoprolol, nadolol, oxprenolol, pindolol, propanolol.

Cardiac inotropic agents: aminone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Cough suppressants: codeine phosphate dexomethorphan, guaifenesin, pholcodine, diamorphine, methadone.

Cytotoxics: ifosfamide, chlorambucil, melphalan, busulphan, cytotoxic antibodies, doxorubicin, epirubicin, plicamycin, bleomycin, methotrexate, cytarabine, fludarabine, gencitabine, fluorouracil, mercaptopurine, thioguanine, vincristine, vinblastine, vindesine, etoposide.

Decongestants: pseudoephedrine hydrochloride.

Diuretics: acetazolamide, amiloride, bendrofluazide, bumetanide, chlorothiazide, chlorthalidone, ethacrynic acid, frusemide, metolazone, spironolactone, triamterene.

Enzymes: pancreatin, pepsin, lipase.

Epilepsy: Gabapentin

Anti-parkinsonian agents: bromocriptine mesylate, lysuride maleate, selegiline, para-fluoroselegiline, lazabemide, rasagiline, 2-BUMP [N-(2-butyl)-N-methylpropargylamine], M-2-PP [N-methyl-N-(2-pentyl)-propargylamine], MDL-72145 [beta-(fluoromethylene)-3,4-dimethoxy-benzeneethanamine], mofegiline, apomorphine, N-propylnoraporphine, cabergoline, metergoline, naxagolide, pergolide, piribedil, ropinirole, terguride, quinagolide.

Gastro-intestinal agents: bisacodyl, cimetidine, cisapride, diphenoxylate HCl, domperidone, metoclopramide, famotidine, loperamide, mesalazine, nizatidine, esomeprazole, metopimazine, pantoprazole, ondansetron HCl, Granisetron, tropisetron, dolasetron, ranitidine HCl, sulphasalazine. Lanzoprazole, Histamine Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Hormone replacement therapy: dydrogesterone

Hypertension: Enalapril

Lactation: Oxytocin, oxytocin agonists

Lipid regulating agents: bezafibrate, clofibrate, fenofibrate, gemfibrozil, probucol.

Local anaesthetics: amethocaine, amylocalne, benzocaine, bucricaine, bupivacaine, butacaine, butanilicaine, butoxycaine, butyl aminobenzoate, carticaine, chloroprocaine, cinchocaine, clibucaine, clormecaine, coca, cocaine, cyclomethycaine, dimethisoquin, diperodon, dyclocalne, ethyl chloride, ethyl p-piperidinoacetylaminobenzoate, etidocaine, hexylcaine, isobutamben, ketocaine, lignocaine, mepivacaine, mepsrylcaine, myrtecaine, octacaine, oxethazaine, oxybuprocaine, parethoxycaine, pramoxine, prilocalne, procaine, propranocaine, propoxycaine, proxymetacaine, ropivacaine, tolycaine, tricaine, trimecaine, vadocaine.

Motion sickness: diphenhydramine

Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamins, such as vitamin A, vitamin $B_2$, vitamin D, vitamin E, vitamin K, minerals.

Opioid analgesics: codeine, dextropropyoxyphene, diamorphine, dihydrocodeine, meptazinol, methadone, morphine, nalbuphine, pentazocine.

Oral vaccines: to prevent or reduce the symptoms of diseases such as Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Traveller's Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhegic Fever, Caries, Chagas Disease, Urinary Tract Infection caused by *E. coli*, Pneumococcal Disease, Mumps, Chikungunya, Hayfever, Asthma, Rheumatoid Arthritis, Carcinomas, Coccidiosis, Newcastle Disease, Enzootic pneumonia, Feline leukemia, Atrophic rhinitis, Erysipelas, Foot and Mouth disease and Swine pneumonia, or to prevent or reduce the symptoms of diseases caused by *Vibrio* species, *Salmonella species*, *Bordetella* species, *Haemophilus* species, *Toxoplasmosis gondii*, *Cytomegalovirus*, *Chlamydia* species, *Streptococcal* species, Norwalk Virus, *Escherischia coli*, *Helicobacter pylori*, Rotavirus, *Neisseria gonorrhae*, *Neisseria meningiditis*, Adenovirus, Epstein Barr Virus, Japanese Encephalitis Virus, *Pneumocystis carini*, Herpes simplex, *Clostridia* species, Respiratory Syncytial Virus, *Klebsiella* species, *Shigella* species, *Pseudomonas aeruginosa*, *Parvovirus*, *Campylobacter* species, *Rickettsia* species, *Varicella zoster*, *Yersinia* species, Ross River Virus, J.C. Virus, *Rhodococcus equi*, *Moraxella catarrhalis*, *Borrelia burgdorferi* and *Pasteurella haemolytica*.

Voiding dysfunctions: Tamsulosine, trospium chloride, tolterodine oxybutinin

Proteins, peptides and recombinant drugs: recombinant hormones and iso-hormones, recombinant cytokines, recombinant plasminogens, TNF receptor fusion protein, monoclonal antibodies, nucleic acids, antisense oligonucleotides, oligonucleotides, glycoproteins and adhesion molecules.

Veterinary Arthritis: Tepoxalin

Sex hormones and Contraceptives: clomiphene citrate, danazol, desogestrel, ethinyloestradiol, ethynodiol, ethynodiol diacetate, levonorgestrel, medroxyprogesterone acetate, mestranol, methyltestosterone, norethisterone, norethisterone enanthate, norgestrel, estradiol, conjugated estrogens, dydrogesterone, progesterone, stanozolol, stilboestrol, testosterone, tibolone.

Schizoprenia; Olanzapine, Nicergoline

Sexual dysfunction: Cabergolin, oxytocin, tadalafil, sildenafil, vardenafil

Spermicides: nonoxynol 9.

Stimulants: amphetamine, dexamphetamine, dexfenfluramine, fenfluramine, mazindol, pemoline.

In a specific, non-limiting embodiment, the active ingredient is desmopressin acetate. In this embodiment the dosage form can be used in voiding postponement or in the treatment or prevention of incontinence, primary nocturnal enuresis (PNE), nocturia or central diabetes insipidus. In one embodiment, the amount of desmopressin acetate in the composition comprises 0.01-2.75% w/w. In another embodiment, the amount of desmopressin acetate in the composition comprises 0.06-2.00% w/w.

In a specific, non-limiting embodiment, the active ingredient is loratidine. In this embodiment the dosage form can e.g. be used for the relief of nasal or non-nasal symptoms of allergic rhinitis and chronic idiopathic urticaria. In one embodiment, the amount of loratidine in the composition comprises 15-20% w/w. In another embodiment, the amount of loratidine in the composition comprises about 19% w/w.

In a specific, non-limiting embodiment, the active ingredient is famotidine. In this embodiment the dosage form can e.g. be used in the treatment of gastroesophageal reflux disease, duodenal and gastric ulcer, pathological hypersecretory conditions (e.g. Zollinger-Ellison syndrome and multiple endocrine adenomas). In one embodiment, the amount of famotidine in the composition comprises 20-90% w/w. In another embodiment, the amount of famotidine in the composition comprises 30-85% w/w.

In a specific, non-limiting embodiment, the active ingredient is montelukast sodium. In this embodiment the dosage form can e.g. be used in prophylaxis and chronic treatment of asthma, allergic rhinitis and exercise-induced bronchoconstriction. In one embodiment, the amount of montelukast sodium in the composition comprises 5-30% w/w. In another embodiment, the amount of montelukast sodium in the composition comprises 10-25% w/w.

A pharmaceutical dosage form of the invention disintegrates, thereby releasing the active ingredient, upon contact with a fluid (an aqueous medium or saliva).

Typically, a pharmaceutical dosage form of the invention is an orodispersible pharmaceutical dosage form which disintegrates in the mouth within 10 seconds or less.

The term "orodispersible" as used herein should be understood to encompass a solid dosage form which disintegrates or dissolves in the mouth within (at most) 10 seconds. In further embodiments, the orodispersible dosage form disperses in the mouth within 9, 8, 7, 6, 5, 4, 3, 2, or even within 1 second.

Suitable route of administration for the dosage form of the subject invention is oral administration including buccal and sublingual administration. In a specific embodiment, the dosage form is administered sublingually. Dosage forms of the invention may also be placed on the tongue or against the cheek or gingiva.

Pharmaceutical dosage forms of the present invention are adapted to supply the active ingredient to e.g. the oral cavity. The active may be absorbed across the mucosa at the site of administration, e.g. sublingual mucosa, and/or otherwise, in the case of oral administration, from the oral cavity (e.g. across the buccal and/or gingival mucosa) and/or from the gastrointestinal tract for systemic distribution.

The exact dose and regimen of administration of the dosage form will necessarily be dependent upon the therapeutic effect to be achieved and may vary with the particular active ingredient, the route of administration, and the age and condition of the individual subject to whom the medicament is to be administered. At times patients may be instructed to take two or any other number of unit dosage forms in a single administration or at times only a portion, such as half or a quarter of the unit dosage form in a single administration.

The dosage form of the invention achieves a balance of performance: stability and fast disintegration. It may be produced by known lyophilisate technology. It can be stored (and packed) in blisters. The invention achieves these results in a single processing step, without the need to resort to multiple steps including granulation.

In addition to the ingredients previously discussed, the matrix may also include other excipients (auxiliary agents, accessory agents) such as, but not limited to fillers, matrix-forming agents, thickeners (including but not limited to guar gum and xanthum gum), binders, diluents, lubricants, pH adjusting agents, protecting agents, viscosity enhancers, wicking agents, non-effervescent disintegrants, effervescent disintegrants, surfactants, anti-oxidants, wetting agents, colorants, flavouring agents, taste-masking agents, sweeteners, preservatives and so forth.

In one embodiment, a composition of the invention is obtainable by subliming solvent from a liquid preparation comprising an active ingredient, inulin and optionally secondary matrix forming agent(s) in a solvent. Typically, the liquid preparation is placed in a mould, e.g. such that following sublimation a solid composition, typically in a dosage unit, is formed within the mould. A mould can be an open blister pack whereby the solid dosage unit is formed within the blister pack's depression which is thereafter sealed by a sealing film or foil.

In one embodiment, the process comprises introducing unit dosage quantities of said preparation into depressions of an open blister pack; and then subliming the preparation to obtain solid dosage forms within said depressions.

The sublimation can be carried out by freeze drying the preparation comprising the active ingredient, inulin and optionally secondary matrix forming agent(s) in a solvent. In one embodiment, the solvent is water.

The invention thus discloses a process for preparing fast-dispersing dosage forms by lyophilizing a combination of an active ingredient, inulin and optionally secondary matrix forming agent(s). The fast-dispersing dosage form contains a network of the active ingredient and the carrier inulin, the network having been obtained by subliming solvent from liquid preparation that contains the active ingredient, inulin and other optional matrix forming agents, Said preparation may be a solution, suspension or dispersion.

Typically, an initial preparation comprising an active ingredient, inulin and optionally secondary matrix forming agent(s) in a solvent is prepared followed by sublimation. The sublimation can be carried out by freeze drying the preparation In a freeze drying procedure, the preparation (in liquid form) that comprises an active ingredient, inulin and any other optional matrix forming agent in a solvent is filled into moulds. Each mould typically contains a defined amount of such solution with a defined amount of active ingredient. The preparation in the mould is then frozen, for example by passing gaseous cooling medium over the mould. After the preparation has been frozen, the solvent is sublimed therefrom. The sublimation is carried out in a freeze dryer. In consequence an open matrix network of inulin optionally together with other matrix forming agents included in the solution, carrying the active ingredient, is thereby formed.

The preparation is contained in a mould during the freeze-drying process to produce a solid form in any desired shape. Prior to the lyophilization, the mould may be cooled and frozen (e.g. in a fast-freeze tunnel or on the shelves of the lyophilizer), for example using liquid nitrogen or solid carbon dioxide.

After lyophilization, the freeze dried compositions can either be removed from the mould if desired or stored therein until later use. Typically, each mould is so designed so to produce a unit dosage form of the composition. The composition so obtained is fast-dispersing and disintegrates within 10 seconds upon contact with fluid.

The solvent can be water but can optionally contain a co-solvent (such as an alcohol e.g. tert-butyl alcohol) to improve the solubility of the chemical.

The composition may contain a pH adjusting agent to adjust the pH of a solution from which the dosage form is prepared within the range of from 2 to 10, typically from 3.5 to 9.5 or from 4.5 to 8. Citric acid, sodium hydroxide, and sodium carbonate are used as pH adjusting agent, but others including hydrochloric acid and malic acid can also be used. Non-volatile pH adjusting agents will not be removed by freeze drying or other sublimation processes and so may be present in the final product.

The mould may comprise a series of cylindrical or other shape depressions in it, each of a size corresponding to a desired size of a dosage form to be formed.

In one embodiment, the mould is a depression in a sheet of filmic material. The filmic material may contain more than one depression. The filmic material may be similar to that employed in conventional blister packs which are used for packaging oral contraceptive tablets and like medicament forms. For example the filmic material may be made of thermoplastic material with the depressions formed by thermoforming or coldforming. Polyvinyl chloride film can be used as filmic material. Laminates of filmic material may also be used.

EXAMPLES

The invention is further described in the following examples, which are not in any way intended to limit the scope of the inventions as claimed.

A) Materials Used in the Examples Presented Below

| Material | Obtained from |
|---|---|
| Inulin (from chicory root) | Beneo Orafti, Belgium |
| Citric acid | Merck, India |
| Mannitol | Merck, India |
| Desmopressin Acetate | Manufactured by Polypeptide Labs A/s, and supplied by Ferring |
| Loratadine | Ultratech India Ltd |
| Famotidine | Exim Pharma International, India |
| Montelukast Sodium | MSN Pharma Chem Pvt. Ltd., India |
| Guar gum | Merck, India |
| Xanthan gum | SD Fine Chem Ltd., India |
| Sodium citrate | Merck, India |
| Pullulan | Hyashibara, Japan |
| Glycine | Sigma Aldrich |
| Hydropropyl methyl cellulose (HPMC) | Shin-Etsu Chemical Co. Japan |
| Methyl cellulose | Shin-Etsu Chemical Co. Japan |
| Gum tragacanth | Merck, India |
| Neotame | Nutrasweet, USA |
| Cherry flavour | Virginia Dare, USA |

B) Method for Preparing Placebo Formulation

1) Dissolve Inulin and other excipients if present in purified water under stirring at 200-500 rpm.
2) Adjust the pH of the solution using citric acid solution or NaOH.
3) Make up the final volume of the solution using purified water.
4) Mix the solution under stirring at 200 to 500 rpm for further 15 min.
5) Dose the solution into each cavity of preformed blister sheets (preferably using dispensing pipette).
6) Freeze the filled blisters at a temperature in the range of −20 to −110° C.
7) Freeze dry the blisters in a lyophilizer.
8) Place the blister sheet containing dried lyophilisates on the punched carrier web of the blister packaging machine to transport the blister sheets through the sealing station of the packaging machine.
9) Seal the blister with a lidding foil and punch into final blisters.

C) Formulations

The following formulations were prepared using the method described in the method section "B" herein above.

Example 1

| Component | Amount/unit | % w/w |
|---|---|---|
| Inulin | 25 mg | 100 |
| Purified water | q.s to 250 μl | — |

Example 2

| Component | Amount | % w/w |
|---|---|---|
| Inulin | 12.5 mg | 50 |
| Mannitol | 12.5 mg | 50 |
| Purified water | q.s to 250 μl | — |

Example 3

| Component | Amount | % w/w |
|---|---|---|
| Inulin | 12.5 mg | 49.99 |
| Mannitol | 12.5 mg | 49.99 |
| Citric acid (5% w/v) | q.s to pH 4.5 | q.s to pH 4.5 |
| Purified water | q.s to 250 μl | — |

Example 4

| Component | Amount | % w/w |
|---|---|---|
| Inulin | 18.75 mg | 49.99 |
| Mannitol | 18.75 mg | 49.99 |
| Citric acid (5% w/v) | q.s to pH 4.5 | q.s to pH 4.5 |
| Purified water | q.s to 250 µl | — |

Example 5

| Component | Amount | % w/w |
|---|---|---|
| Inulin | 18.75 mg | 74.99 |
| Raffinose | 6.25 mg | 24.99 |
| Citric acid (5% w/v) | q.s to pH 4.5 | q.s to pH 4.5 |
| Purified water | q.s to 250 µl | — |

Example 6

| Component | Amount | % w/w |
|---|---|---|
| Inulin | 18.75 mg | 74.99 |
| Trehalose | 6.25 mg | 24.99 |
| Citric acid (5% w/v) | q.s to pH 4.5 | q.s to pH 4.5 |
| Purified water | q.s to 250 µl | — |

Example 7

| Component | Amount | % w/w |
|---|---|---|
| Inulin | 37.5 mg | 100 |
| Purified water | q.s to 250 µl | — |

Example 8

| Component | Amount | % w/w |
|---|---|---|
| Inulin | 37.5 mg | 99.99 |
| Citric acid (5% w/v) | q.s to pH 4.5 | q.s to pH 4.5 |
| Purified water | q.s to 250 µl | — |

Example 9

| Component | Amount | % w/w |
|---|---|---|
| Inulin | 37.5 mg | 71.39 |
| Mannitol | 15 mg | 28.59 |
| Citric acid (5% w/v) | q.s to pH 4.5 | q.s to pH 4.5 |
| Purified water | q.s to 250 µl | — |

D) Method for Preparing Dosage Forms Containing Desmopressin

1) Dissolve Inulin and other excipients in purified water under stirring at 200-500 rpm
2) Dissolve Desmopressin acetate in purified water and add to the solution prepared in step 1.
3) Adjust the pH of the solution using citric acid solution (5% w/v).
4) Make up the final volume of the solution using purified water.
5) Mix the solution under stirring at 200 to 500 rpm for further 15 min.
6) Dose the solution into cavities of preformed blister sheets (preferably using dispensing pipette).
7) Freeze the filled blisters at a temperature in the range of −20 to −110° C.
8) Freeze dry the blisters in a lyophilizer
9) Place the blister sheet containing dried lyophilisates on the punched carrier web of the blister packaging machine to transport the blister sheets through the sealing station of the packaging machine.
10) Seal the blister with a lidding foil and punch into final blisters.

E) Desmopressin Formulations

The following desmopressin lyophilisate formulations were prepared using the method described in "D" herein above.

Example 10

| Component | Amount/unit | % w/w |
|---|---|---|
| Desmopressin acetate equivalent to Desmopressin | 240 µg | 0.63 |
| Inulin | 37.5 mg | 99.36 |
| Citric acid (5% w/v) | q.s to pH 4.5 | q.s to pH 4.5 |
| Purified water | q.s to 250 µl | — |

Example 11

| Component | Amount/unit | % w/w |
|---|---|---|
| Desmopressin acetate equivalent to Desmopressin | 240 µg | 0.45 |
| Inulin | 37.5 mg | 71.10 |
| Mannitol | 15 mg | 28.44 |
| Citric acid (5% w/v) | q.s to pH 4.5 | q.s to pH 4.5 |
| Purified water | q.s to 250 µl | — |

Example 12

| Component | Amount/unit | % w/w |
|---|---|---|
| Desmopressin acetate equivalent to Desmopressin | 240 µg | 0.63 |
| Inulin | 37.5 mg | 99.36 |
| Citric acid (5% w/v) | q.s to pH 4.0 | q.s to pH 4.0 |
| Purified water | q.s to 250 µl | — |

Example 13

| Component | Amount/unit | % w/w |
|---|---|---|
| Desmopressin acetate equivalent to Desmopressin | 240 μg | 0.95 |
| Inulin | 12.5 mg | 49.52 |
| Mannitol | 12.5 mg | 49.52 |
| Sodium Citrate Buffer (2.5 mM) | q.s to pH 4.8 | q.s to pH 4.8 |
| Purified water | q.s to 250 μl | — |

Example 14

| Component | Amount/unit | % w/w |
|---|---|---|
| Desmopressin acetate equivalent to Desmopressin | 240 μg | 0.95 |
| Inulin | 12.5 mg | 49.52 |
| Mannitol | 12.5 mg | 49.52 |
| Citric acid (5% w/v) | q.s to pH 4.3 | q.s to pH 4.3 |
| Purified water | q.s to 250 μl | — |

Example 15

| Component | Amount/unit | % w/w |
|---|---|---|
| Desmopressin acetate equivalent to Desmopressin | 60 μg | 0.24 |
| Inulin | 12.5 mg | 49.88 |
| Mannitol | 12.5 mg | 49.88 |
| Citric acid (5% w/v) | q.s to pH 4.3 | q.s to pH 4.3 |
| Purified water | q.s to 250 μl | — |

Example 16

| Component | Amount/unit | % w/w |
|---|---|---|
| Desmopressin acetate equivalent to Desmopressin | 25 μg | 0.09 |
| Inulin | 12.5 mg | 49.95 |
| Mannitol | 12.5 mg | 49.95 |
| Citric acid (5% w/v) | q.s to pH 4.3 | q.s to pH 4.3 |
| Purified water | q.s to 250 μl | — |

Example 17

| Component | Amount/unit | % w/w |
|---|---|---|
| Desmopressin acetate equivalent to Desmopressin | 10 μg | 0.04 |
| Inulin | 12.5 mg | 49.98 |
| Mannitol | 12.5 mg | 49.98 |
| Citric acid (5% w/v) | q.s to pH 4.3 | q.s to pH 4.3 |
| Purified water | q.s to 250 μl | — |

Example 18

| Component | Amount/unit | % w/w |
|---|---|---|
| Desmopressin acetate equivalent to Desmopressin | 240 μg | 0.95 |
| Inulin | 12.5 mg | 49.52 |
| Mannitol | 12.5 mg | 49.52 |
| Purified water | q.s to 250 μl | — |

Example 19

| Component | Amount/unit | % w/w |
|---|---|---|
| Desmopressin acetate equivalent to Desmopressin | 240 μg | 0.56 |
| Inulin | 30.0 mg | 70.19 |
| Mannitol | 12.5 mg | 29.24 |
| Sodium Citrate Buffer (2.5 mM) | q.s to pH 4.8 | q.s to pH 4.8 |
| Purified water | q.s to 250 μl | — |

Example 20

| Component | Amount/unit | % w/w |
|---|---|---|
| Desmopressin acetate equivalent to Desmopressin | 240 μg | 0.56 |
| Inulin | 30.0 mg | 70.19 |
| Mannitol | 12.5 mg | 29.24 |
| Sodium Citrate Buffer (2.5 mM) | q.s to pH 5.0 | q.s to pH 5.0 |
| Purified water | q.s to 250 μl | — |

Example 21

| Component | Amount/unit | % w/w |
|---|---|---|
| Desmopressin acetate equivalent to Desmopressin | 240 μg | 0.53 |
| Inulin | 30.0 mg | 66.31 |
| Mannitol | 12.5 mg | 27.63 |
| Pullulan | 2.5 mg | 5.52 |
| Sodium Citrate Buffer (2.5 mM) | q.s to pH 4.8 | q.s to pH 4.8 |
| Purified water | q.s to 250 μl | — |

Example 22

| Component | Amount/unit | % w/w |
|---|---|---|
| Desmopressin acetate equivalent to Desmopressin | 240 μg | 0.53 |
| Inulin | 30.0 mg | 66.31 |
| Mannitol | 12.5 mg | 27.63 |
| Pullulan | 2.5 mg | 5.52 |
| Sodium Citrate Buffer (2.5 mM) | q.s to pH 5.0 | q.s to pH 5.0 |
| Purified water | q.s to 250 μl | — |

Example 23

| Component | Amount/unit | % w/w |
|---|---|---|
| Desmopressin acetate equivalent to Desmopressin | 240 μg | 0.86 |
| Inulin | 12.5 mg | 45.06 |
| Mannitol | 12.5 mg | 45.06 |
| Pullulan | 2.5 mg | 9.01 |
| Citric acid (5% w/v) | q.s to pH 4.3 | q.s to pH 4.3 |
| Purified water | q.s to 250 μl | — |

F) Method for Preparing Dosage Forms Containing Loratadine

1) Disperse gums in purified water under stirring at 200-500 rpm.
2) Prepare solution of inulin and other excipients in water under stirring at 200-500 rpm, and add this solution in the gum solution obtained in step 1 under stirring.
3) Add loratadine to the solution obtained in step 2 under continuous stirring to obtain a suspension.
4) Homogenize the Loratadine suspension for 20 min to form uniform suspension.
5) Adjust the pH of the suspension using citric acid solution (5% w/v).
6) Make up the final volume of the suspension using purified water.
7) Mix the suspension under stirring at 200 to 500 rpm for further 15 min.
8) Dose prepared suspension into each cavity of preformed blister sheets with intermediate stirring of the suspension to maintain uniformity.
9) Freeze the filled blisters at a temperature in the range of −20 to −110° C.
10) Freeze dry the blisters in a lyophilizer.
11) Place the blister sheet containing dried lyophilisates on the punched carrier web of the blister packaging machine to transport the blister sheets through the sealing station of the packaging machine.
12) Seal the blister with a lidding foil and punch into final blisters.

G) Loratadine Formulations

The following Loratidine lyophilisate formulations were prepared using the method described in "F" herein above.

Example 24

| Component | Amount/unit | % w/w |
|---|---|---|
| Loratadine | 10 mg | 19.89 |
| Inulin | 37.5 mg | 74.59 |
| Mannitol | 2.4 mg | 4.77 |
| Xanthan gum | 0.375 mg | 0.74 |
| Citric acid (5% w/v) | q.s to pH 4.3 | q.s to pH 4.3 |
| Purified water | q.s to 250 μl | — |

Example 25

| Component | Amount/unit | % w/w |
|---|---|---|
| Loratadine | 10 mg | 19.86 |
| Inulin | 37.5 mg | 74.48 |
| Mannitol | 2.4 mg | 4.76 |
| Guar gum | 0.45 mg | 0.89 |
| Citric acid (5% w/v) | q.s to pH 4.3 | q.s to pH 4.3 |
| Purified water | q.s to 250 μl | — |

H) Method for Preparing Dosage Forms Containing Famotidine

1) Disperse guar gum in purified water under stirring at 200-500 rpm.
2) Dissolve inulin and other excipients in the solution obtained in step 1 under stirring at 200-500 rpm.
3) Add Famotidine to the solution of step 2 under continuous stirring till proper suspension is formed.
4) Homogenize the Famotidine suspension obtained in step 3 for 10 min to form uniform suspension.
5) Make up the final volume of the suspension using purified water.
6) Mix the suspension under stirring at 200 to 500 rpm for further 15 min.
7) Dose prepared suspension into each cavity of preformed blister sheets with intermediate stirring of the suspension to maintain uniformity.
8) Freeze the filled blisters at a temperature in the range of −20 to −110° C.
9) Freeze dry the blisters in a lyophilizer
10) Place the blister sheet containing dried lyophilisates on the punched carrier web of the blister packaging machine to transport the blister sheets through the sealing station of the packaging machine.
11) Seal the blister with a lidding foil and punch into final blisters.

I) Famotidine Formulations

The following Famotidine lyophilisate formulations were prepared using the method described in "H" herein above.

Example 26

| Component | Amount/unit | % w/w |
|---|---|---|
| Famotidine | 40 mg | 81.80 |
| Inulin | 5 mg | 10.22 |
| Mannitol | 3 mg | 6.13 |
| Guargum | 0.90 mg | 1.84 |
| Purified water | q.s 250 μl | — |

Example 27

| Component | Amount/unit | % w/w |
|---|---|---|
| Famotidine | 20 mg | 32.57 |
| Inulin | 37.5 mg | 61.08 |
| Mannitol | 3 mg | 4.88 |

-continued

| Component | Amount/unit | % w/w |
|---|---|---|
| Guargum | 0.90 mg | 1.46 |
| Purified water | q.s 250 µl | — |

J. Method for Preparing Dosage Forms Containing Montelukast

1) Dissolve Montelukast sodium in purified water under stirring at 200-500 rpm.
2) Dissolve Inulin and other excipients in the Montelukast solution of step 1 under stirring at 200-500 rpm.
3) Make up the final volume of the solution using purified water.
4) Mix the solution under stirring at 200 to 500 rpm for further 15 min.
5) Dose the solution into each cavity of preformed blister.
6) Freeze the filled blisters at a temperature in the range of −20 to −110° C.
7) Freeze dry the blisters in a lyophilizer
8) Place the blister sheet containing dried lyophilisates on the punched carrier web of the blister packaging machine to transport the blister sheets through the sealing station of the packaging machine.
9) Seal the blister with a lidding foil and punch into final blisters.

K. Montelukast Formulations

The following montelukast orodispersible dosage forms were prepared using the method described in "3" above.

Example 28

| Component | Amount/unit | % w/w |
|---|---|---|
| Montelukast sodium equivalent to Montelukast | 10 mg | 21.05 |
| Inulin | 37.5 mg | 78.94 |
| Purified water | q.s to 250 µl | — |

Example 29

| Component | Amount/unit | % w/w |
|---|---|---|
| Montelukast sodium equivalent to Montelukast | 10 mg | 19.04 |
| Inulin | 37.5 mg | 71.42 |
| Mannitol | 5 mg | 9.52 |
| Purified water | q.s to 250 µl | — |

Example 30

| Component | Amount/unit | % w/w |
|---|---|---|
| Montelukast sodium equivalent to Montelukast | 10 mg | 24.27 |
| Inulin | 20 mg | 48.54 |
| Mannitol | 10 mg | 24.27 |
| Xanthan gum | 0.5 mg | 1.21 |
| Neotame | 0.2 mg | 0.48 |
| Cherry flavour | 0.5 mg | 1.21 |
| Purified water | q.s to 250 µl | — |

Example 31

| Component | Amount/unit | % w/w |
|---|---|---|
| Montelukast sodium equivalent to Montelukast | 4 mg | 11.48 |
| Inulin | 20 mg | 57.44 |
| Mannitol | 10 mg | 28.72 |
| Xanthan gum | 0.5 mg | 1.43 |
| Neotame | 0.12 mg | 0.34 |
| Cherry flavour | 0.2 mg | 0.57 |
| Purified water | q.s to 250 µl | — |

Example 32

| Component | Amount/unit | % w/w |
|---|---|---|
| Montelukast sodium equivalent to Montelukast | 5 mg | 13.96 |
| Inulin | 20 mg | 55.83 |
| Mannitol | 10 mg | 27.92 |
| Xanthan gum | 0.5 mg | 1.39 |
| Neotame | 0.12 mg | 0.33 |
| Cherry flavour | 0.2 mg | 0.56 |
| Purified water | q.s to 250 µl | — |

L) Comparative Examples

Example 33

Comparative lyophilisates were prepared according to the method described in "B" herein above, but using Pullulan in place of inulin.

| Component | Amount/unit | % w/w |
|---|---|---|
| Pullulan | 25 mg | 100 |
| Purified water | q.s 250 µl | — |

Example 34

Comparative lyophilisates were prepared according to the method described in "B" herein above, but using HPMC in place of inulin.

| Component | Amount/unit | % w/w |
|---|---|---|
| HPMC | 25 mg | 100 |
| Purified water | q.s 250 µl | — |

Example 35

Comparative lyophilisates were prepared according to the method described in "B" herein above, but using methyl cellulose in place of inulin.

| Component | Amount/unit | % w/w |
|---|---|---|
| Methyl cellulose | 25 mg | 100 |
| Purified water | q.s 250 µl | — |

Example 36

Comparative lyophilisates were prepared according to the method described in "B" herein above, but using gum tragacanth in place of inulin.

| Component | Amount/unit | % w/w |
|---|---|---|
| Gum tragacanth | 25 mg | 100 |
| Purified water | q.s 250 µl | — |

Example 37

Comparative lyophilisates were prepared according to the method described in "B" herein above, but using fish gelatin in place of inulin.

| Component | Amount/unit | % w/w |
|---|---|---|
| Fish gelatin | 25 mg | 100 |
| Purified water | q.s 250 µl | — |

Example 38

Comparative lyophilisates were prepared according to the method described in "B" herein above, but using fish gelatin in place of inulin.

| Component | Amount/unit | % w/w |
|---|---|---|
| Fish gelatin | 12.5 mg | 50 |
| Mannitol | 12.5 mg | 50 |
| Purified water | q.s 250 µl | — |

M) Disintegration Tests

Ma) Disintegration Test in Petri Dish

This test measures the expected disintegration time of a composition of the invention in an aqueous medium which is an indication of its disintegration time in saliva.

The disintegration rate of the lyophilisates on a wet filter paper was determined according to the method described in WO2009002084 page 12 paragraph 129, wherein the test was performed at a temperature of about 25±2° C.

Mb) Measurement of Oral Dissolving Time (ODT) of Placebo

The dissolving time of the placebo lyophilisates in the oral cavity was determined according to the method described in PCT application WO2009002084, page 12 paragraph 132, wherein the lyophilisate was placed on the tongue of a healthy human adult and then measuring the time for it to completely dissolve while rubbing the lyophilisates between the tongue and the upper palate. The mean ODT was calculated from the data obtained from 5 healthy human adults.

N) Method for Testing Disintegration Time (Invitro DT)

This test measures the disintegration time of the compositions of the invention in aqueous medium which is an indication of their disintegration time in saliva.

Equipment: Electrolab, Model: ED2 SAPO

Procedure:

The method was followed as per USP 31-NF 26 (General Chapters, <701>Disintegration) and Ph Eur. 1997 (2.9.1. Disintegration of tablets and capsules).

Water was filled into the beaker and maintained at 37° C.±0.5° C. using water bath. The lyophilisates were placed in sinker made up of copper wire with diameter of about 0.5 mm (±0.05 mm) and length of about 15 mm. The lyophilisates were then place into the basket of basket rack assembly and instrument was set on. The disintegration time was noted in seconds.

O) Dissolution Method

This test measures the dissolution (%) of an active ingredient from a composition of the invention in aqueous medium which is an indication of the release rate of the active ingredient from the composition.

Equipment: Varian, Model: VK7025

Procedure:

The method was followed as per USP 32-NF 27 (General Chapters, <711>Dissolution). Dissolution media (0.1N HCl, Phosphate buffer pH 6.8, Acetate buffer pH 4.5, or 0.5% SLS in water) was selected on the basis of the active ingredient in the composition. Dissolution bowls were filled with appropriate media volume (500 mL and 900 mL) on the basis of the active ingredient in the composition and the temperature of the media was maintained at 37° C.±0.5° C. using water bath. The apparatus used was USP type II (Paddle) and set at the required rpm (50 rpm) as per the test procedure. Samples were withdrawn as per the time point (5 min, 10 min, 15 min, and 30 min) defined in the test procedure. Samples were analysed chromatographically or by UV as per the test procedure and % release was calculated.

The disintegration rates, ODT, in-vitro DT and Dissolution data for the lyophilisates prepared according to examples 1 to 18, and comparative example 19 to 24 are given in table 1.

TABLE 1

| Example No | Disintegration test in petri dish (sec) | Oral dissolving time (sec) | In-vitro DT (sec) | Dissolution (5/15 minutes) (%) |
|---|---|---|---|---|
| 1 | 1 | 3 | 1 | NA |
| 2 | 2 | 2 | 1 | NA |
| 3 | 1 | 2 | 2 | NA |
| 4 | 2 | 2 | 2 | NA |
| 5 | 1 | 1 | 1 | NA |
| 6 | 1 | 1 | 1 | NA |
| 7 | 2 | 3 | 1 | NA |
| 8 | 3 | 3 | 1 | NA |
| 9 | 2 | 4 | 1 | NA |
| 10 | 1 | NA | 1 | 80/85 |

TABLE 1-continued

| Example No | Disintegration test in petri dish (sec) | Oral dissolving time (sec) | In-vitro DT (sec) | Dissolution (5/15 minutes) (%) |
|---|---|---|---|---|
| 11 | 1 | NA | 1 | 96/95 |
| 12 | 1 | NA | 2 | 98/99 |
| 13 | 3 | NA | 3 | 98/99 |
| 14 | 2 | NA | 2 | 98/99 |
| 15 | 2 | NA | 2 | 92/96 |
| 16 | 2 | NA | 2 | 89/95 |
| 17 | 2 | NA | 2 | 100/102 |
| 18 | 3 | NA | 3 | 96/97 |
| 19 | 3 | NA | 3 | 70/86 |
| 20 | 3 | NA | 2 | 98/99 |
| 21 | 2 | NA | 3 | 99/101 |
| 22 | 3 | NA | 2 | 96/101 |
| 23 | 3 | NA | 3 | 102/102 |
| 24 | 4 | NA | 3 | 96/105 |
| 25 | 7 | NA | 2 | 103/113 |
| 26 | 5 | NA | 8 | 70/85 |
| 27 | 5 | NA | 6 | 78/91 |
| 28 | 4 | NA | 2 | 95/95 |
| 29 | 4 | NA | 2 | 100/99 |
| 30 | 4 | NA | 2 | 96/96 |
| 31 | 2 | NA | 2 | 89/92 |
| 32 | 5 | NA | 3 | 106/106 |
| 33 | 32 | 30 | 196 | NA |
| 34 | 35 | 51 | 128 | NA |
| 35 | >300 | 192 | >30 minutes | NA |
| 36 | 36 | 30 | 20 | NA |
| 37 | 2 | 5 | <2 | NA |
| 38 | 2 | 4 | <2 | NA |

NA—Not applicable for column 3 as the oral dissolving time was measured for placebo lyophilisates only.
NA—Not applicable for column 5 as the dissolution time was measured for lyophilisates containing drug substances only.

The invention claimed is:

1. A pharmaceutical composition comprising:
   (a) at least one matrix-forming agent that is inulin to form an open matrix network, wherein the inulin ranges from 30% to 80% of the entire weight of the composition; and
   (b) at least one pharmaceutically active ingredient chosen from desmopressin, desmopressin acetate, loratidine, famotidine, montelukast sodium, and ondansetron HCl carried by the open matrix network,
   wherein at least 80% of the pharmaceutical composition dissolves within 10 seconds upon contact with an aqueous solution.

2. The pharmaceutical composition according to claim 1, further comprising one or more secondary matrix-forming agents.

3. The pharmaceutical composition according to claim 2, wherein the one or more secondary matrix forming agents is selected from the group consisting of trehalose, raffinose, and mannitol.

4. The pharmaceutical composition according to claim 3, wherein the one or more secondary matrix-forming agent is mannitol.

5. The pharmaceutical composition according to claim 1, wherein the at least one pharmaceutically active ingredient is desmopressin.

6. The pharmaceutical composition according to claim 1, wherein the at least one pharmaceutically active ingredient is desmopressin acetate.

7. The pharmaceutical composition according to claim 1, wherein the at least one pharmaceutically active ingredient is loratidine.

8. The pharmaceutical composition according to claim 1, wherein the at least one pharmaceutically active ingredient is famotidine.

9. The pharmaceutical composition according to claim 1, wherein the at least one pharmaceutically active ingredient is montelukast sodium.

10. The pharmaceutical composition according to claim 1, wherein the at least one pharmaceutically active ingredient is ondansetron HCl.

11. The pharmaceutical composition according to claim 1, wherein the composition rapidly disintegrates upon contact with saliva.

12. A pharmaceutical composition prepared by a process comprising at least a step of sublimating a solvent from a liquid preparation that comprises:
   (a) at least one matrix forming agent that is inulin, wherein the inulin ranges from 30% to 80% of the entire weight of the composition; and
   (b) at least one pharmaceutically active ingredient chosen from desmopressin, desmopressin acetate, loratidine, famotidine, montelukast sodium, and ondansetron HCl.

13. The pharmaceutical composition according to claim 12, wherein the at least one pharmaceutically active ingredient is desmopressin.

14. The pharmaceutical composition according to claim 12, wherein the at least one pharmaceutically active ingredient is desmopressin acetate.

15. The pharmaceutical composition according to claim 12, wherein the at least one pharmaceutically active ingredient is loratidine.

16. The pharmaceutical composition according to claim 12, wherein the at least one pharmaceutically active ingredient is famotidine.

17. The pharmaceutical composition according to claim 12, wherein the at least one pharmaceutically active ingredient is montelukast sodium.

18. The pharmaceutical composition according to claim 12, wherein the at least one pharmaceutically active ingredient is ondansetron HCl.

19. The pharmaceutical composition according to claim 12, wherein the liquid preparation further comprises one or more secondary matrix-forming agents.

20. The pharmaceutical composition according to claim 12, wherein the one or more secondary matrix forming agents is mannitol.

21. A pharmaceutical composition comprising:
   (a) a first matrix forming agent that is inulin, wherein the inulin ranges from 30% to 80% of the entire weight of the composition and, optionally, a second matrix forming agent selected from the group consisting of trehalose, raffinose, and mannitol, to form an open matrix network; and
   (b) at least one pharmaceutically active ingredient chosen from desmopressin, desmopressin acetate, loratidine, famotidine, montelukast sodium, and ondansetron HCl carried by the open matrix network,
   wherein at least 80% of the pharmaceutical composition dissolves within 10 seconds upon contact with an aqueous solution.

22. The pharmaceutical composition according to claim 21, wherein the at least one pharmaceutically active ingredient is desmopressin.

23. The pharmaceutical composition according to claim 21, wherein the at least one pharmaceutically active ingredient is desmopressin acetate.

24. The pharmaceutical composition according to claim 1, wherein the at least one pharmaceutically active ingredient is loratidine.

25. The pharmaceutical composition according to claim 21, wherein the at least one pharmaceutically active ingredient is famotidine.

26. The pharmaceutical composition according to claim 21, wherein the at least one pharmaceutically active ingredient is montelukast sodium.

27. The pharmaceutical composition according to claim 21, wherein the at least one pharmaceutically active ingredient is ondansetron HCl.

28. A blister pack having one or more depressions disposed therein, wherein each of the one or more depressions comprises a pharmaceutical composition, the pharmaceutical composition comprises:
 (a) at least one matrix-forming agent that is inulin to form an open matrix network; and
 (b) at least one pharmaceutically active ingredient chosen from desmopressin, desmopressin acetate, loratidine, famotidine, montelukast sodium, and ondansetron HCl carried by the open matrix network.

29. The blister pack according to claim 28, which is prepared by a process which comprises the steps of:
 (a) introducing a liquid preparation into one or more depressions of a blister pack, the liquid preparation comprising the matrix forming agent and the pharmaceutically active ingredient; and
 (b) sublimating a solvent from the liquid preparation in the one or more depressions.

30. The blister pack according to claim 28, wherein the open matrix network further comprises one or more secondary matrix-forming agents.

31. The blister pack according to claim 30, wherein the one more secondary matrix-forming agents is selected from the group consisting of trehalose, raffinose, and mannitol.

32. The blister pack according to claim 31, wherein the one or more secondary matrix-forming agent is mannitol.

33. The blister-pack according to claim 28, wherein the at least one pharmaceutically active ingredient is desmopressin.

34. The blister pack according to claim 28, wherein the at least one pharmaceutically active ingredient is desmopressin acetate.

35. The blister pack according to claim 28, wherein the at least one pharmaceutically active ingredient is loratidine.

36. The blister pack according to claim 28, wherein the at least one pharmaceutically active ingredient is famotidine.

37. The blister pack according to claim 28, wherein the at least one pharmaceutically active ingredient is montelukast sodium.

38. The blister pack according to claim 28, wherein the at least one pharmaceutically active ingredient is ondansetron HCl.

* * * * *